(12) United States Patent
Kohn

(10) Patent No.: US 10,954,357 B2
(45) Date of Patent: Mar. 23, 2021

(54) PRODUCT AND METHOD FOR A PLASTIC COMPOSITION COMPRISING INORGANIC MATERIALS

(71) Applicant: Steve Kohn, Short Hills, NJ (US)

(72) Inventor: Steve Kohn, Short Hills, NJ (US)

( * ) Notice: Subject to any disclaimer, the term of this patent is extended or adjusted under 35 U.S.C. 154(b) by 0 days.

(21) Appl. No.: 15/380,991

(22) Filed: Dec. 15, 2016

(65) Prior Publication Data
US 2017/0292004 A1    Oct. 12, 2017

Related U.S. Application Data

(63) Continuation-in-part of application No. 15/093,187, filed on Apr. 7, 2016.

(60) Provisional application No. 62/322,844, filed on Apr. 15, 2016, provisional application No. 62/386,895, filed on Dec. 15, 2015, provisional application No. 62/387,102, filed on Dec. 21, 2015.

(51) Int. Cl.
| | |
|---|---|
| *C08K 3/26* | (2006.01) |
| *C08L 23/06* | (2006.01) |
| *C08L 61/20* | (2006.01) |
| *B32B 27/18* | (2006.01) |
| *B65D 33/04* | (2006.01) |
| *A61G 13/10* | (2006.01) |
| *A61G 7/05* | (2006.01) |
| *B65D 65/38* | (2006.01) |
| *A61B 46/00* | (2016.01) |
| *C08K 3/013* | (2018.01) |
| *A61B 90/90* | (2016.01) |
| *A61B 50/30* | (2016.01) |
| *B65D 33/00* | (2006.01) |
| *A45C 3/00* | (2006.01) |
| *B65D 33/06* | (2006.01) |
| *B65D 65/46* | (2006.01) |
| *B65D 33/28* | (2006.01) |

(52) U.S. Cl.
CPC .............. *C08K 3/26* (2013.01); *A45C 3/001* (2013.01); *A61B 46/00* (2016.02); *A61G 7/05* (2013.01); *A61G 13/10* (2013.01); *B32B 27/18* (2013.01); *B65D 33/004* (2013.01); *B65D 33/065* (2013.01); *B65D 33/28* (2013.01); *B65D 65/38* (2013.01); *B65D 65/466* (2013.01); *C08K 3/013* (2018.01); *C08L 23/06* (2013.01); *C08L 61/20* (2013.01); *A61B 46/40* (2016.02); *A61B 50/30* (2016.02); *A61B 90/90* (2016.02); *B65D 2203/00* (2013.01); *C08K 2003/265* (2013.01); *C08L 2201/06* (2013.01); *C08L 2205/025* (2013.01); *C08L 2205/03* (2013.01); *C08L 2207/062* (2013.01); *C08L 2207/066* (2013.01)

(58) Field of Classification Search
CPC .. C08L 23/06; C08L 23/0815; C08L 2205/02; C08L 2205/03; C08L 2666/02; Y10T 2666/02
USPC .......................... 428/35.5; 524/849, 847, 700
See application file for complete search history.

(56) References Cited

U.S. PATENT DOCUMENTS

| | | | |
|---|---|---|---|
| 4,770,912 A * | 9/1988 | Furrer ..................... | C08L 23/06 428/35.5 |
| 2008/0213521 A1* | 9/2008 | Halahmi ................. | C08L 23/06 428/35.7 |

* cited by examiner

*Primary Examiner* — William K Cheung
(74) *Attorney, Agent, or Firm* — Weiss; Philip Weiss

(57) ABSTRACT

Products and methods for producing products which comprise polyethylene and inorganic minerals for a single layer plastic composition.

36 Claims, 9 Drawing Sheets

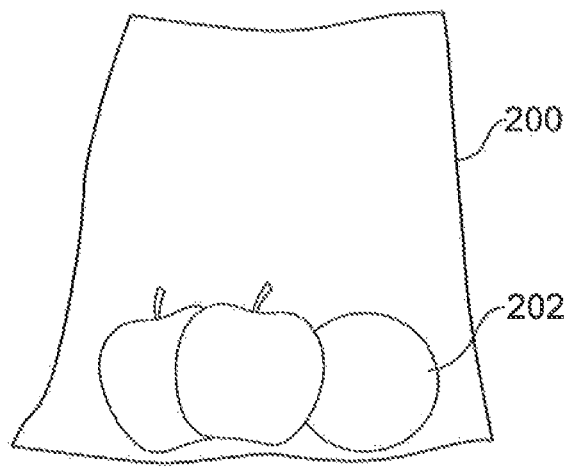
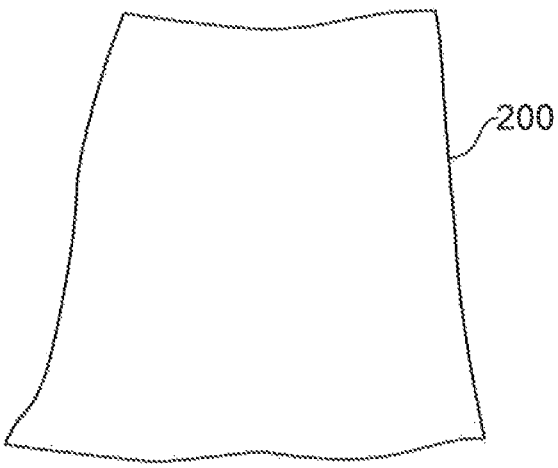
FIG. 11A  FIG. 11B
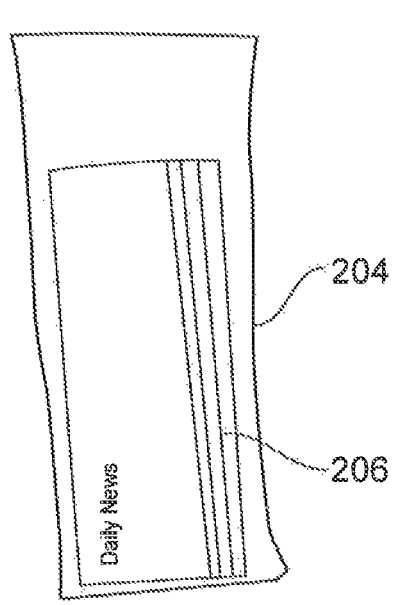
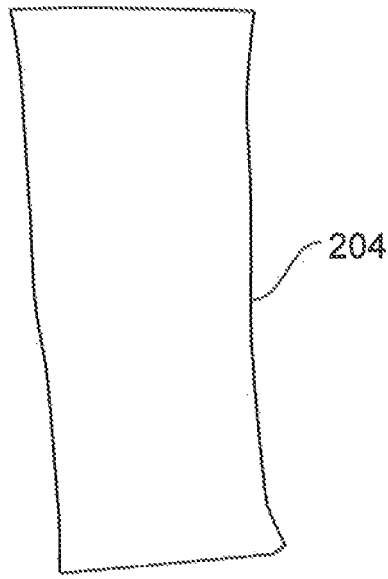
FIG. 12A  FIG. 12B

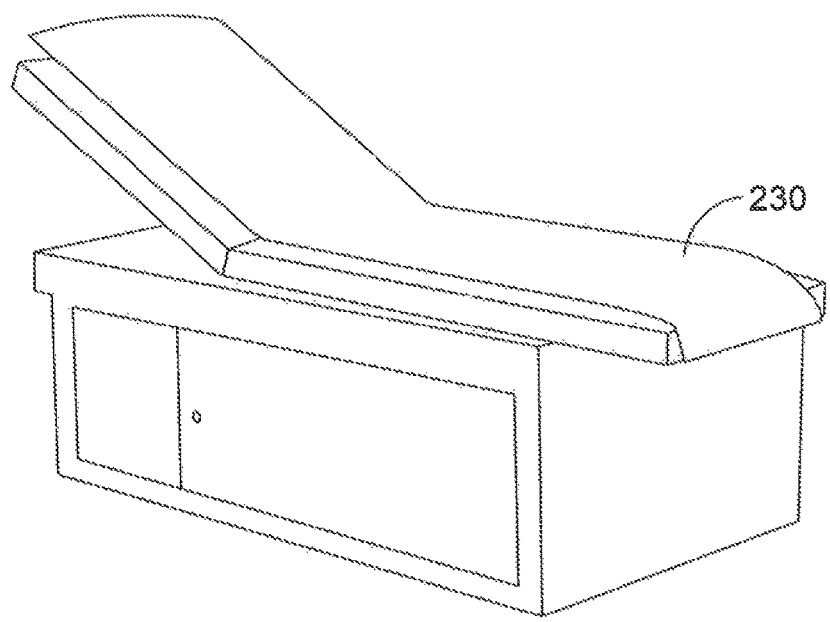
FIG. 22
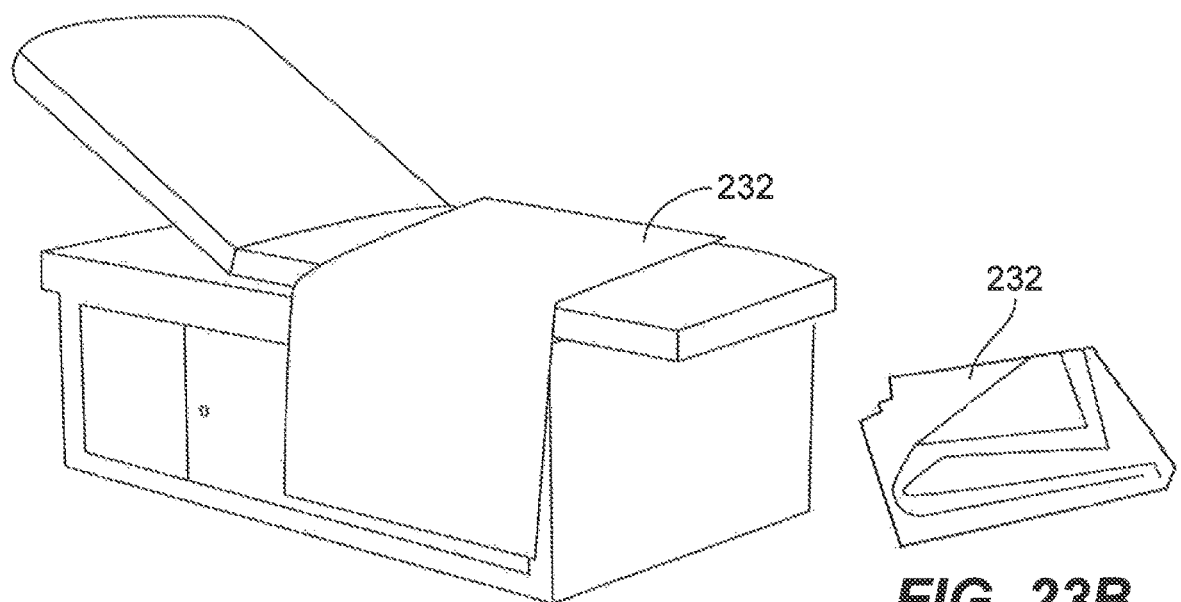
FIG. 23A  FIG. 23B

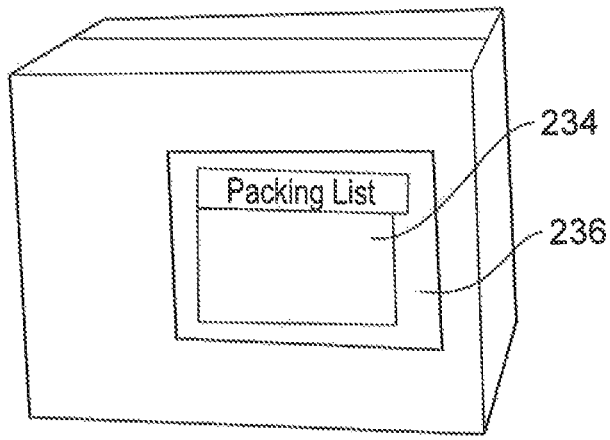
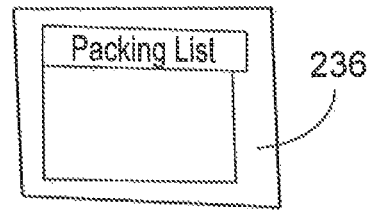
FIG. 24A
FIG. 24B
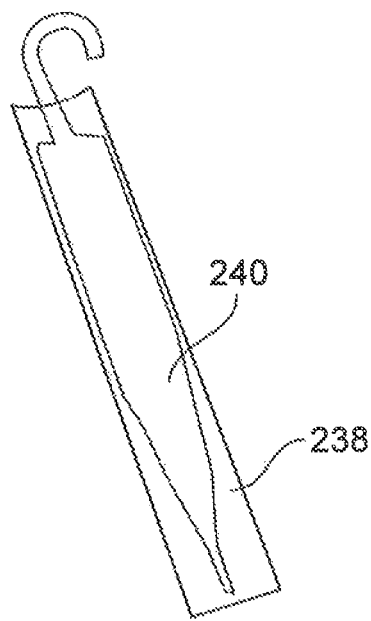
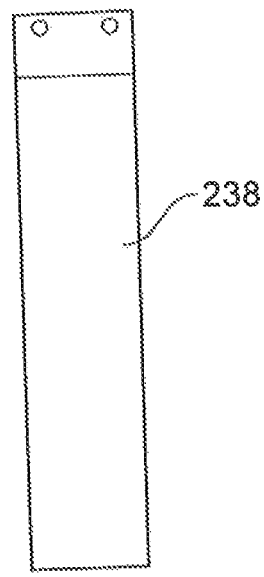
FIG. 25A
FIG. 25B

PRODUCT AND METHOD FOR A PLASTIC COMPOSITION COMPRISING INORGANIC MATERIALS

RELATED APPLICATIONS

The present application is a continuation in part of U.S. patent application Ser. No. 15/093,187 filed Apr. 7, 2016 and is related to Provisional application Ser. No. 62/322,844 filed Apr. 15, 2016, Provisional application Ser. No. 62/386,895 filed Dec. 15, 2015 and Provisional Application Ser. No. 62/387,102 filed Dec. 21, 2015.

FIELD OF THE INVENTION

The present invention relates to products and a method of producing products which comprise polyethylene and inorganic minerals for a single layer plastic composition.

BACKGROUND OF THE INVENTION

Printed and unprinted flexible and semi-rigid packaging materials are commonly used for packing retail, industrial, and commercial products into plastic bags such as T-sacks, sacks, pouches, wrappers and the like. Desired product features of plastic compositions include printability and different levels of opacity. Since some plastic products may be used in a sterile environment, sterilization may also be a required step in the manufacturing process.

The amount and type of resin used, and the thickness, material weight and density of the materials all affect the cost and other characteristics of the plastic compositions. Key performance attributes of these materials include substantial barrier protection, product protection and containment, shipping, storage, and dispensing applications. Barrier protection refers to the ability of a packaging material to stop or retard the passage of atmospheric gases or water vapor into the material from the outside environment. The prior art uses metalizing to provide a lustrous metallic appearance, that when applied to plastic film, improves gas and light barrier properties of the film.

Polyethylene (PE) film has been used in the prior art on preparation of plastic compositions because of its transparency, toughness, heat seal-ability, low water vapor transmission rate, low temperature performance and low cost. PE films are highly permeable to oxygen and other non-polar gases and have high viscoelastic flow properties.

Polypropylene (PP) film is a transparent, tough, thermoplastic film. Un-oriented film is soft and becomes brittle at low temperature, however this property as well as strength, stiffness, and clarity can be improved by orientation e.g. bi-axially oriented polypropylene (BOPP). Polystyrene film is a transparent, stiff film of high permeability and moderate temperature resistance that can be oriented to improve strength. Films can also be made of polyamide (PA). PA is used almost entirely as a film or sheet material in packaging applications. The clear film offers a good oxygen barrier, and is particularly tough and abrasion resistant. However, PA film is a poor moisture barrier, does not heat seal, and has cost disadvantages. Films can also be made of polychlorotrifluoroethylene (PCTFE or CTFE), which is a plastic material characterized by exceptional moisture and good oxygen barrier characteristics as well as good clarity.

A problem that exists with prior films is that these products do not incorporate low cost, environmentally friendly materials and designs. Environmentally friendly materials can have desirable attributes such as biodegradability, compostability, and recyclability, and may also use less energy, pollute less, and generate fewer greenhouse gases in their manufacture than previous materials. Such environmentally friendly materials are increasingly in demand from consumers and retailers.

Another significant problem that exists with prior flexible film packaging is the high concentration of expensive plastic and polymers required to achieve the performance specifications needed. Yet another problem is the very expensive combinations of plastics, foils, coatings, and metalized films to achieve structural, barrier, sealing and printability aspects.

U.S. Pat. No. 8,507,581 relates to a stone based copolymer substrate which includes calcium carbonate from approximately 50-85% by weight varying in size generally from 1.0 to 3.0 microns; HDPE from approximately 2-25% by weight; and a biopolymer from approximately 2-25% by weight. The biopolymer may include a polymer of lactic acid (PLA), polyhydroxybutanoate (PHB), polyhydroxyalkanoates (PHA), Nylon 611 and Poly lactic Acid.

U.S. Pat. No. 8,569,411 is directed to flexible packaging composites which include one or more mineral-containing layers with thermoplastic bonding agent. The composite may also contain one or more non-mineral containing layers, including various combinations of extruded resins, cast or blown films, and fibers. The mineral-containing layer is substantially and continuously bonded to the other layers. The polymer, fiber and mineral containing layers can be made such that the resulting composite structure formed is machined to form a storage article. The specification provides that the bonding agents can include, but are not limited to, HDPE, and another bonding agent that is a high molecular weight high density polyethylene. The film composite comprises: at least one mineral-containing layer containing a thermoplastic bonding agent in an amount of about 15-30% by weight and a mineral material that is present in an amount of about 70-85% by weight. The film composite comprises: at least one mineral-containing layer bonded to said at least one non mineral-containing layer, said at least one mineral-containing layer containing a thermoplastic bonding agent in an amount of about 15-30% by weight and a mineral material that is present in an amount of about 70-85% by weight. The film composite comprises: at least one minerals containing layer that is at least 0.5 mil in caliper containing a thermoplastic bonding agent in an amount of about 15-30% by weight and a mineral content that is present in an amount of about 70-85% by weight.

U.S. Pat. No. 8,177,066 is directed to a high visual impact plastic packaging, wherein plasticized or laminated paperboard materials can be used, as well as plastic materials such as mineral-based materials, poly lactic acid, and recycled or recyclable polyurethane. The packaging is created into separate portions that include blister portions, cavity portions, windows and holes, and compacted regions.

U.S. Pat. No. 9,062,190 is directed to a stone based copolymer substrate which includes calcium carbonate from approximately 50-85% by weight and varying in size generally from 1.0 to 3.0 microns; HDPE from approximately 2-25% by weight; and a biopolymer from approximately 2-25% by weight.

U.S. Patent Publication 2013/0227881 is directed to a recycled plastic composite composition which includes a recycled EVA 30% to 80% by weight and a stone powder from 20% to 70% by weight.

U.S. Patent Publication 2009/0047499 is directed to a multi-layer composite structure and storage article made therefrom, which includes a fiber-containing layer, such as a fiberboard layer or other layer having fibers from natural or synthetic sources, and a ground calcium carbonate-containing layer covering the fiber-containing layer. The extruded calcium carbonate containing layer comprising at least 30% by weight of the thermoplastic bonding agent.

U.S. Patent Publication 2009/0047511 is directed to a multi-layer composite material structure and storage article made therefrom which includes a fiber-containing layer, such as fiberboard layer or other layer having fibers from natural or synthetic sources, and a mineral-containing layer covering the fiber-containing layer.

U.S. Patent Publication 2009/0142528 is directed to a composite structure having at least two layers, comprising less than 25% Polymers, a fiber-containing layer, such as a layer of paperboard or other layer having fibers from natural or synthetic sources, and a mineral-containing layer covering and bonded to the fiber-containing layer.

US. Patent Publication 2014/0057061 is directed to flexible packaging composites having at least two layers which include one or more mineral-containing layers with a thermoplastic bonding agent. A flexible film composite suitable for use as a packaging material for storage of articles, comprising: at least one mineral-containing layer containing a thermoplastic bonding agent and a mineral material. The mineral containing layer is an external most layer of the flexible film composite. The mineral material is selected from the group consisting of ground calcium carbonate, diatomaceous earth, mica, silica, glass, zeolite, slate, and combinations thereof, and at least one layer adhered to the at least one mineral-containing layer by a wet or dry lamination technique. The mineral-containing layer and the at least one other layer form a composite material that is flexible. The mineral material is present in the mineral-containing layer in an amount of up to 85% by weight. The at least one other layer comprises a non-mineral containing layer selected from the group consisting of ink, nylon, a sealant, foil, oriented polypropylene (OPP), metalized oriented polypropylene (OPP), polypropylene, polypropylene terephthalate (PET), a peel and stick label backing, polyethylene, ethylene-vinyl alcohol (EVOH), paper, a fiber material coated with polyethylene, a fiber containing layer, a biodegradable polymer, a photodegradable polymer, and a polyester. The at least one mineral containing layer is sterilizable.

U.S. Patent Publication 2014/0272352 is directed to a composite structure which includes at least one or more fiber-containing layers and one or more mineral-containing layers. The mineral-containing layer comprises a thermoplastic bonding agent fixing the minerals in place. A recyclable composite packaging material, comprising: a fiber-containing layer, and a mineral-containing layer bonded to the fiber-containing layer. The mineral-containing layer comprises a thermoplastic bonding agent and has a mineral content of 20-70 wt %; and wherein thickness and composition of the mineral containing layer are selected to provide a screen cleanliness efficiency of 60% to 100% and a removal efficiency of the mineral containing layer from the fiber-containing layer of 50% to 95% by mass in a repulping recycling operation.

U.S. Patent Publication 2014/0274632 is directed to a composite structure including a fiber-containing layer, such as a fiberboard layer or other layer having fibers from natural and/or synthetic sources, and a mineral-containing layer covering the fiber-containing layer. A composite packaging material, comprising: one or more mineral-containing layer extrusion bonded to a fiber-containing layer; wherein the mineral-containing layer is formed from a mineral containing polymer comprising a polymer composition and a mineral composition.

U.S. Patent Publication 2014/0274633 is directed to a composite structure having at least two layers, including a fiber-containing layer, such as a fiberboard layer or other layer having fibers from natural and/or synthetic sources, and a mineral-containing layer covering the fiber-containing layer.

SUMMARY OF INVENTION

The present invention relates to the use of a plastic material in combination with environmentally stable materials. The environmentally stable materials are inorganic mineral compounds.

It is an object of the present invention for the inorganic mineral compound to be a calcium carbonate based material.

The present invention relates to a plastic composition comprising: approximately 20-49% calcium carbonate; approximately 30-60% high density polyethylene; approximately 0-20% linear low density polyethylene; and approximately 0-10% fillers/bonding agent. The plastic composition is a single layer. It is an object of the present invention for the plastic composition to further comprise a biopolymer. It is an object of the present invention for the biopolymer to comprise approximately 0.5% to 20% by weight of the plastic composition. It is an object of the present invention for the plastic composition to further comprise a biopolymer in an amount less than 1.5%. It is an object of the present invention for the biopolymer to be selected from the group consisting of: poly lactic acid, poly-hydroxybutunoate, poly-hydroxyalkanoate, Nylon 610, Nylon 611.

It is an object of the present invention for the plastic composition to contain no fibers. It is an object of the present invention for the external surface of the plastic composition to comprise a printable surface. It is an object of the present invention for the external surface of the plastic composition to comprise a smooth surface. It is an object of the present invention for the plastic composition to provide a moisture barrier.

It is an object for the present invention for the plastic composition to comprise printed information. It is an object of the present invention for the plastic composition to comprise a barcode. It is an object of the present invention for the plastic composition to comprise a coupon.

The present invention relates to a plastic composition comprising: approximately 20-49% mineral material; approximately 30-60% high density polyethylene; approximately 0-20% linear low density polyethylene; approximately 040% fillers/bonding agents. The plastic composition is a single layer.

It is an object of the present invention for the inorganic mineral compounds to comprise calcium carbonate, calcium sulfate, barium sulfate, kaolin, mica, zinc oxide, dolomite, glass fiber, hollow glass microbead, silica, chalk, talc, pigment, titanium dioxide, bentonite, clay, zeolite, slate, diatomaceous earth and combinations thereof.

The present invention relates to a plastic composition comprising: approximately 25-40% calcium carbonate; approximately 30-50% high density polyethylene; approximately 5-15% linear low density polyethylene; and approximately 2-7% filler/bonding agent. The plastic composition is a single layer.

The present invention relates to a plastic composition comprising: approximately 20-49% mineral material; approximately 30-60% high density polyethylene; approximately 0-20% low density polyethylene, linear low density polyethylene or a combination thereof; and approximately 0-10% fillers/bonding agent. The plastic composition is a single layer.

The present invention relates to a plastic composition comprising: calcium carbonate, high density polyethylene, linear low density polyethylene, and a filler/bonding agent. The plastic composition is a single layer. It is an object of the present invention for the calcium carbonate to comprise less than 50% by weight of the composition.

The present invention relates to a plastic composition comprising: calcium carbonate, high density polyethylene; low density polyethylene, linear low density polyethylene or a combination; and a filler/bonding agent. The plastic composition is a single layer. It is an object of the present invention for the calcium carbonate to comprise less than 50% by weight of the composition.

It is an object of the present invention for the calcium carbonate based material to be combined with a non-toxic PE resin. It is an object of the present invention for the polyethylene to comprise high density polyethylene, medium density polyethylene, low density polyethylene, linear low density polyethylene or any combination thereof.

It is an object of the present invention that the single layered products be used for packaging, retail, industrial, and commercial products into plastic bags, sacks, pouches, wrappers, and the like. It is an object of the present invention for the packaging and bags to have printing.

It is an object of the present invention for the formed materials to have a high degree of pliability and flexibility, and to have a printing surface that readily accepts coating and inks. It is an object of the present invention to use these materials to form printed or unprinted plastic compositions. It is an object of the present invention for any of these products to have an antimicrobial component added to it.

It is an object of the present invention for the material to be torn or cut easily so that, for example, a printed coupon can be removed from the material, but strong enough to hold items in the composition.

It is an object of the present invention for the composition to have a matte and a non-glossy finish. It is an object of the present invention for the plastic composition to be smooth to the touch but not slippery. It is an object of the present invention for the plastic composition to be translucent.

It is an object of the present invention to make the environmental friendly plastic materials into different sizes.

It is an object of the present invention for the plastic composition to be made of either HDPE, LLDPE, or LDPE in combination with an inorganic mineral compound.

It is an object of the present invention that the more calcium carbonate based or inorganic material used in the manufacturing of any of the plastic based products, the greater the required mil thickness of the plastic based product in order to preserve the strength, performance and effectiveness of the plastic based product.

It is an object of the present invention for the plastic composition to be formed into a bag. It is an object of the present invention for the plastic composition to be formed into a cover. It is an object of the present invention for the plastic composition to be formed into a sheet. It is an object of the present invention for the plastic composition to be formed into protective garments. It is an object of the present invention for the plastic composition to be formed into school, office and warehousing supplies. It is an object of the present invention for the plastic composition to be wound on a roll. It is an object of the present invention for the plastic composition to be perforated.

It is an object of the present invention to use the composition to form printed or unprinted storage bags. It is an object of the present invention to use the composition to form bags to store food. It is an object of the present invention to use the composition to form bags to store mattresses. It is an object of the present invention to use the composition to form bags to store furniture or other large objects. It is an object of the present invention to use the composition to form bags to store newspapers, magazines and umbrellas. It is an object of the present invention for any of these products to have an antimicrobial component added to it.

It is an object of the present invention for the covers to include such products as chair, sofa, and love seat covers (collectively known as "upholstery covers"). It is an object of the present invention for the covers to include such products as tarps and/or pallet covers. It is an object of the present invention for any of these products to have an antimicrobial component added to it.

It is an object of the present invention for the sheets to include such products as medical examination paper (also known as table paper) and bedding sheets. It is an object of the present invention to use the composition to form soil liners for use by farmers, landscapers, construction workers and both professional and recreational gardeners. It is an object of the present invention for any of these products to have an antimicrobial component added to it.

It is an object of the present invention for the protective garments to include medical products such as adult bibs, capes, exam vests, cover ups, drapes, exam shorts, gowns, pillow cases, ponchos, scrubs, lab coats, and protective head coverings. It is an object of the present invention for any of these products to have an antimicrobial component added to it.

It is an object of the present invention for the plastic composition to be sterilized for use in the medical field, such as medical examination paper.

It is an object of the present invention for the plastic composition to be formed into school, office and warehousing supplies. It is an object of the present invention for the plastic composition to be used to produce a bubble mailer product. It is an object of the present invention to use the composition to form shipping mailing labels with adhesive backing. It is an object of the present invention to use the plastic composition to form packing list plastic envelopes typically used on shipping boxes.

It is an object of the present invention to make the environmentally friendly plastic compositions into different sizes of bags, covers, sheets, protective garments, and school, office and warehousing supplies.

It is an object of the present invention for the plastic composition to form signs.

It is an object of the present invention for the bags, covers, sheets, protective garments, and school, office and warehousing supplies to be made from HDPE, LLDPE, or LDPE in combination with inorganic mineral compounds.

It is an object of the present invention for the materials to be destroyed eventually by exposure to the sun. It is an object of the present invention for the inorganic mineral material layer to be more biodegradable as more inorganic mineral material is added.

It is an object of the present invention for the inorganic mineral to be biodegradable and/or compostable. It is an object of the present invention for the plastic composition to be biodegradable. It is an object of the present invention for the plastic composition to be compostable. It is an object of the present invention for the plastic composition to further comprise a biopolymer. It is an object of the present invention for the biopolymer to comprise poly lactic acid, poly-hydroxybutunoate, poly-hydroxyalkanoates, Nylon 610, or Nylon 611. It is an object of the present invention for the biopolymer to comprise approximately 0.5% to 20% by weight of the plastic composition. It is an object of the present invention for the biopolymer to comprise no more than 1.5% of the plastic composition.

It is an object of the present invention for the filler/bonding agent to comprise a polymer.

It is an object of the present invention for the bonding agent to be photodegradable.

It is an object of the present invention for the composition to comprise at least 30% by weight of inorganic mineral powders. It is an object of the present invention for the rest of the material to comprise polyethylene and fillers, with the majority being polyethylene and less than 5% being fillers. It is an object of the present invention for the composition when used as a plastic material to have the same or equivalent strength as plastic without the inorganic mineral powder, for example, for the plastic materials to have the same or equivalent puncture resistance, tear strength and tensile factor.

The present invention also relates to a plastic packaging composite comprising an inorganic mineral with a bonding agent. It is an object of the present invention for the flexible packaging to be formed into storage bags, protective films, tapes, medical exam paper and other products defined in the present application.

It is an object of the present invention for the plastic composition to have a high degree of pliability and flexibility, and to have a printing surface that readily accepts coating and inks.

It is an object of the present invention for the plastic composition to comprise: nylon, a sealant, oriented polypropylene (OPP), metalized oriented polypropylene, polypropylene, polyethylene terephthalate (PET), polyethylene, ethylene-vinyl alcohol (EVOH).

It is an object of the present invention for the composition to be recyclable.

It is an object of the present invention for the mineral based composition to be biodegradable, photo-degradable, and compostable. It is an object of the present invention for the bonding agent to be photo-degradable.

It is an object of the present invention for the bonding layer to have barrier properties.

It is an object of the present invention for the ground calcium carbonate or other mineral content materials be fabricated from natural sources, such as limestone.

It is an object of the present invention for the single layer mineral containing plastic composition to not include a separate paper layer or a separate plastic layer.

It is an object of the present invention for the composition to be able to be torn for certain uses, for example, medical exam paper, and stretch film. Further, it is an object of the present invention for the composition to be torn or cut such as if a coupon is printed on the material and needs to be torn off.

It is an object of the present invention for the plastic composition to be used to produce mattress bags. It is an object of the present invention for the mattress bags to comprise a thickness of approximately 1.0 to 6 mil. It is an object of the present invention for the mattress bags to have dimensions of 39"-91" by 87"-100" with a gusset of 10"-14". It is an object of the present invention for the mattress bags to comprise a clear polyethylene material. It is an object of the present invention for the material to be water resistant.

It is an object of the present invention for the mattress bags to each be individually folded and bagged. It is an object of the present invention for the mattress bags to be on rolls.

It is an object of the present invention for the plastic composition to be used to produce upholstery covers. It is an object of the present invention for the upholstery covers to comprise a thickness of approximately 1.0 to 6.0 mil. It is an object of the present invention for the upholstery covers to have dimensions of 54"-150" by 42"-52". It is an object of the present invention for the upholstery covers to comprise a clear polyethylene material. It is an object of the present invention for the upholstery covers to comprise an opaque polyethylene material. It is an object of the present invention for the upholstery covers to each be individually folded and bagged. It is an object of the present invention for the upholstery covers to be on rolls.

It is an object of the present invention for the plastic composition to be used to produce a stretch wrap product. It is an object of the present invention for the plastic composition to be approximately a 12 micron/80 gauge equivalent film. It is an object of the present invention for the plastic composition to be placed and dispensed from rolls. It is an object of the present invention for the film to only stick to itself. It is an object of the present invention for the film to tear with the appropriate amount of tension.

It is an object of the present invention for the plastic composition to be used to create a plastic film used for carpet protection. It is an object of the present invention for the film to be stored and distributed off of a roll.

It is an object of the present invention for the plastic composition to be used as a rug storage bag.

It is an object of the present invention for the plastic composition to be used as a plastic portfolio bag. It is an object of the present invention for the plastic portfolio bag to be folded. It is an object of the present invention for the plastic portfolio bag to be stored and distributed off of a roll.

It is an object of the present invention to use the plastic composition for a silverware storage and transport bag.

It is an object of the present invention to use the plastic composition for a cushion storage and transport bag.

BRIEF DESCRIPTION OF DRAWINGS

FIG. 11A is an embodiment of a bag of the present invention showing a food storage bag.

FIG. 11B is an embodiment of a bag of the present invention showing an empty food storage bag.

FIG. 12A is an embodiment of a bag of the present invention showing a newspaper bag.

FIG. 12B is an embodiment of a bag of the present invention showing an empty newspaper bag.

FIG. 22 is an embodiment of the present invention showing examination paper.

FIG. 23A is an embodiment of the present invention showing a drape.

FIG. 23B is an embodiment of the present invention showing a folded drape.

FIG. 24A is an embodiment of the present invention showing a packing list in a plastic envelope attached to a box.

FIG. 24B is an embodiment of the present invention showing the plastic packing list envelope.

FIG. 25A is an embodiment of the present invention showing an umbrella bag with an umbrella.

FIG. 25B is an embodiment of the present invention showing an empty umbrella bag.

FIG. 12A show a newspaper bag 204 having a newspaper 206.

FIG. 12B shows an empty newspaper bag 204.

FIG. 13 shows a tarp cover 208.

FIG. 14 shows a pallet cover 210.

FIG. 15A shows a mattress 212 in a mattress bag 214.

FIG. 15B shows an empty mattress bag 214.

FIG. 16A shows a furniture cover 216 over a sofa 218.

FIG. 16B shows a furniture cover 216.

FIG. 17 shows an examination or medical gown 220.

FIG. 18 shows a lab coat 222.

FIG. 19 shows an examination or medical cape 224.

FIG. 20 shows examination shorts 226.

FIG. 21 shows a poncho 228.

FIG. 22 shows examination paper 230.

FIG. 23A shows a drape 232.

FIG. 23B shows a folded drape 232.

FIG. 24A shows a packing list 234 in a plastic envelope 236 attached to a box.

FIG. 24B shows the plastic packing list envelope 236.

FIG. 25A shows an umbrella bag 238 with an umbrella 240.

FIG. 25B shows an empty umbrella bag 238.

FIG. 26 shows a soil liner 242 in a flower bed or in a garden.

In an embodiment the T-sack and/or T-shirt bags have a width of approximately 5" to 20", a height from 10" to 40" and a gusset from 2" to 15", with thickness ranging from approximately 0.25-4.0 mil.

DETAILED DESCRIPTION OF THE INVENTION

FIGS. 1-4 show embodiments of T-sacks 10-40 of different sizes.

Figure 1:
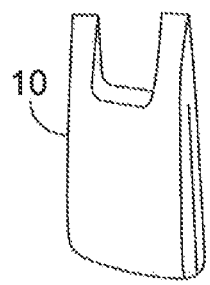
FIG. 1 is an embodiment of a T-sack of the present invention.
Figure 2:
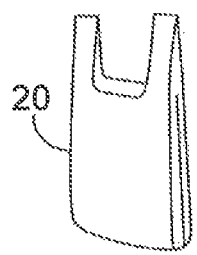
FIG. 2 is an embodiment of a T-sack of the present invention.
Figure 3:
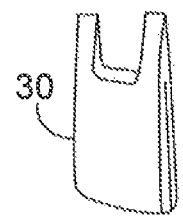
FIG. 3 is an embodiment of a T-sack of the present invention.
Figure 4:
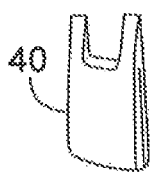
FIG. 4 is an embodiment of a T-sack of the present invention.
Figure 5:
FIG. 5 is an embodiment of a die cut bag of the present invention.

FIG. 5 shows a die cut bag 50.

Figure 6:
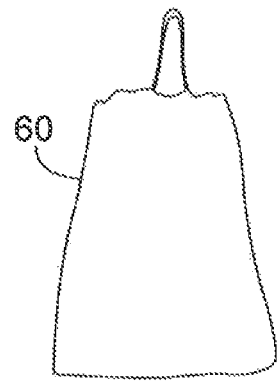
FIG. 6 is an embodiment of a drawstring bag of the present invention.

FIG. 6 shows a drawstring bag 60.

Figure 7:
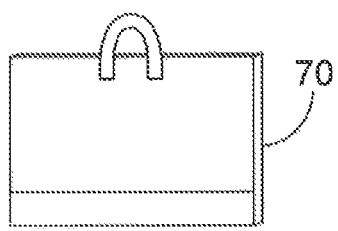
FIG. 7 is an embodiment of a loop handle bag of the present invention.

FIG. 7 shows a loop handle bag 70.

Figure 8:
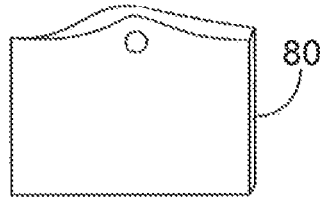
FIG. 8 is an embodiment of a wave style bag of the present invention.

FIG. 8 shows a wave style bag 80.

Figure 9:
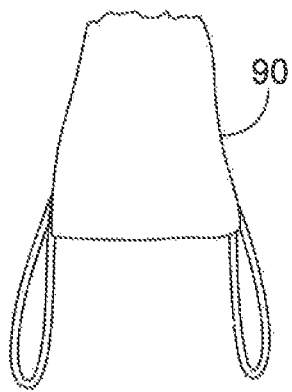
FIG. 9 is an embodiment of a drawstring bag of the present invention.

FIG. 9 shows a drawstring bag 90.

Figure 10:
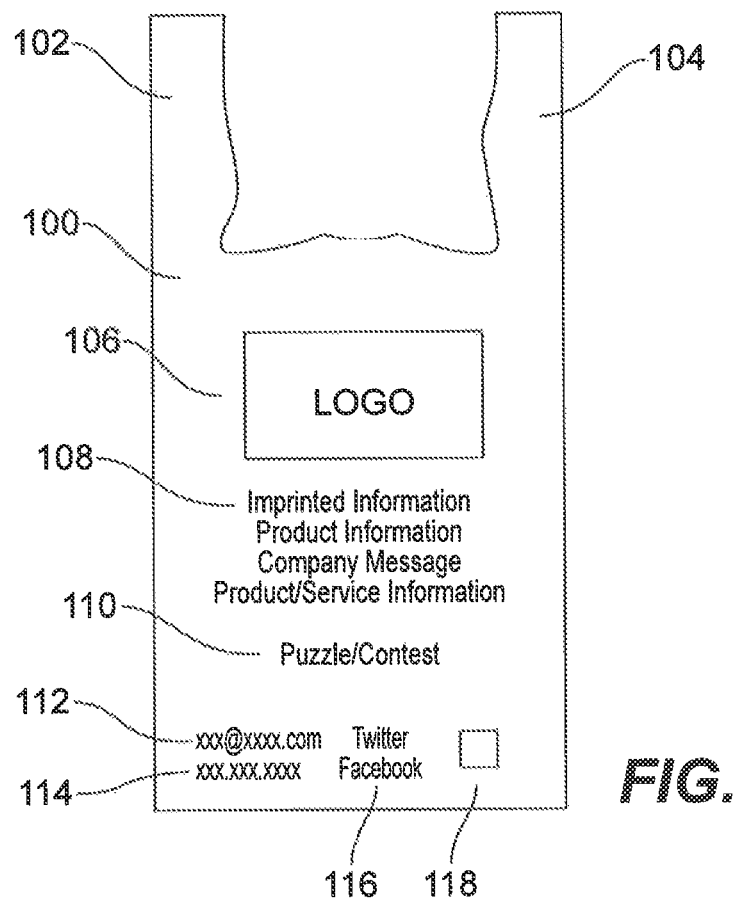
FIG. 10 is a front view of an embodiment of a T-sack of the present invention.

FIG. 10 shows a T-sack 100 having handles 102 and 104; logo 106; printed information, such as a company message, or product or service information 108; a puzzle or contest 110; website information 112; phone number 114; social media link to a portal such as, Twitter or Facebook 116; and QR Code 118.

Figure 11:
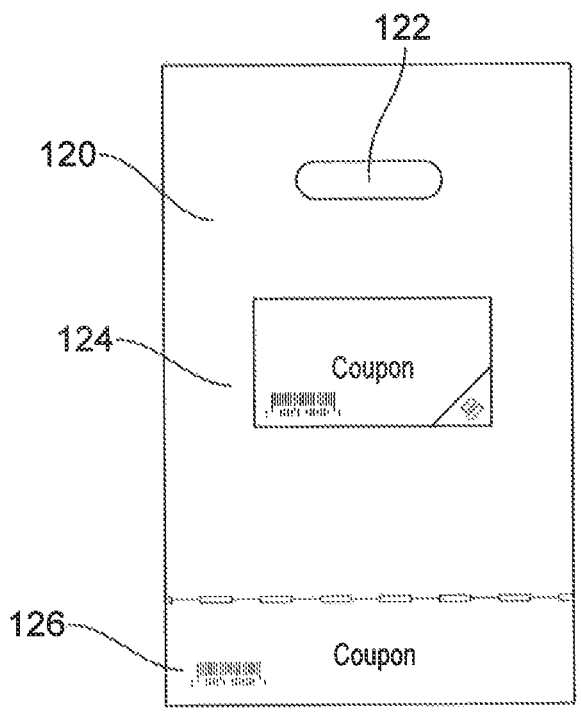
FIG. 11 is a front view of an embodiment of a die cut bag of the present invention.
Figure 13:
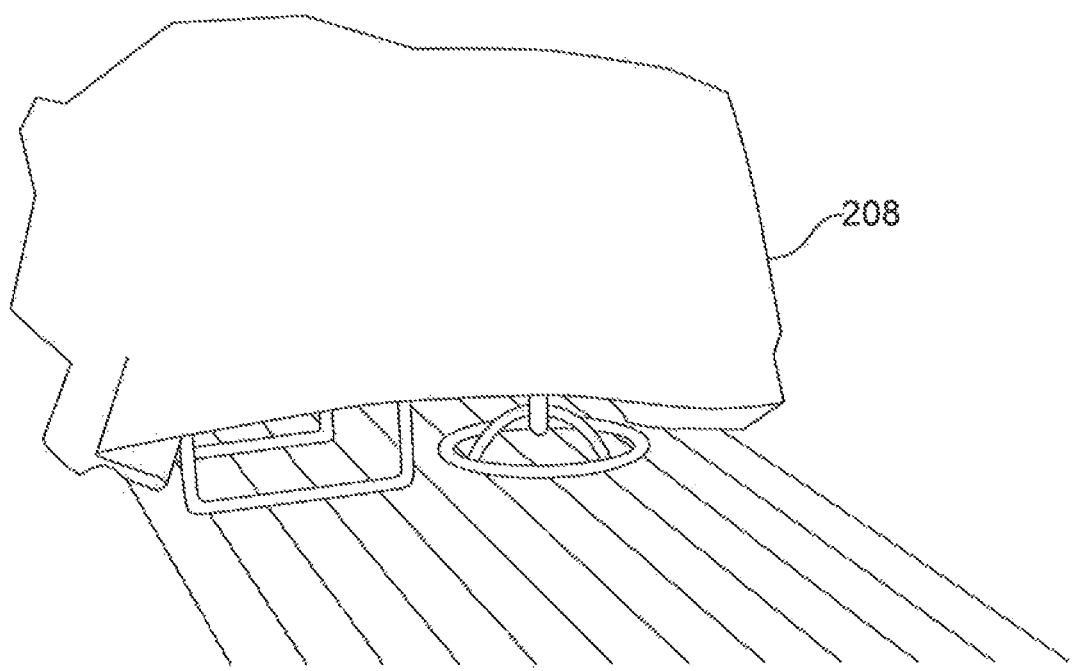
FIG. 13 is an embodiment of the present invention showing a tarp cover.
Figure 14:
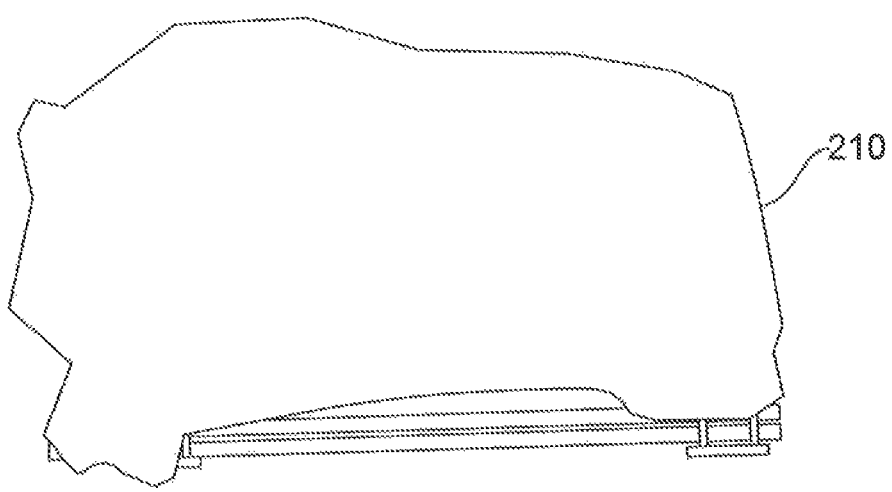
FIG. 14 is an embodiment of the present invention showing a pallet cover.
Figure 15A:
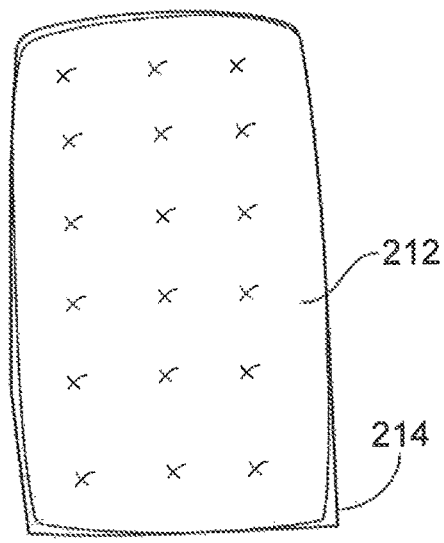
FIG. 15A is an embodiment of the present invention showing a mattress in a mattress bag.
Figure 15B:
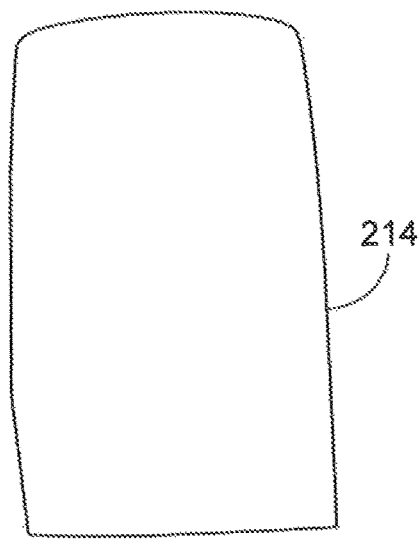
FIG. 15B is an embodiment of the present invention showing an empty mattress bag.
Figure 16A:
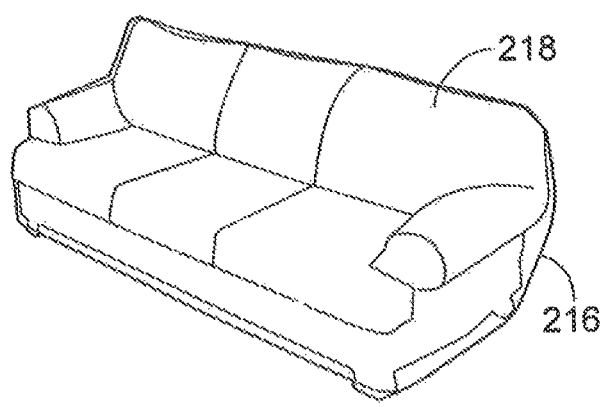
FIG. 16A is an embodiment of the present invention showing a furniture cover over a sofa.
Figure 16B:
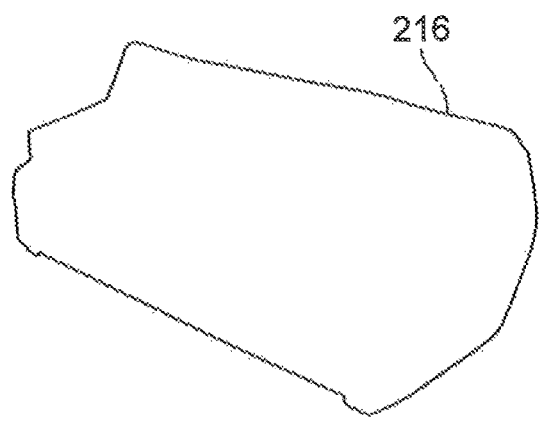
FIG. 16B is an embodiment of the present invention showing a furniture cover.
Figure 17:
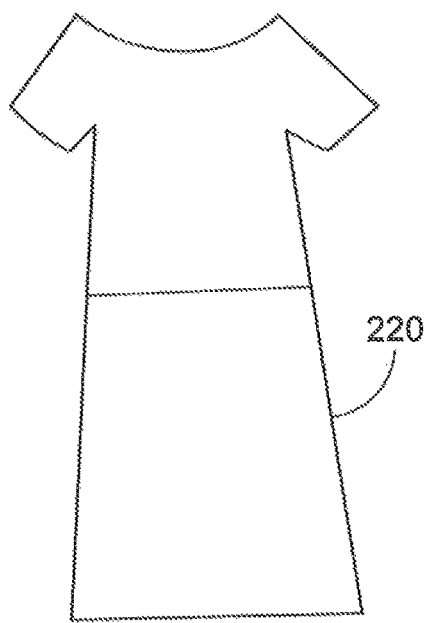
FIG. 17 is an embodiment of the present invention showing an examination or medical gown.
Figure 18:
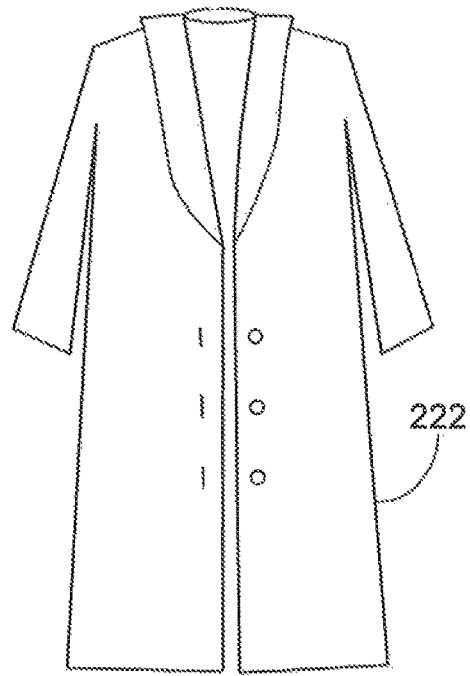
FIG. 18 is an embodiment of the present invention showing a lab coat.
Figure 19:
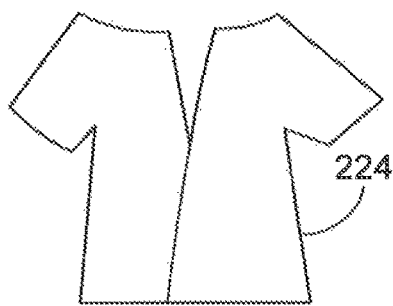
FIG. 19 is an embodiment of the present invention showing an examination or medical cape.
Figure 20:
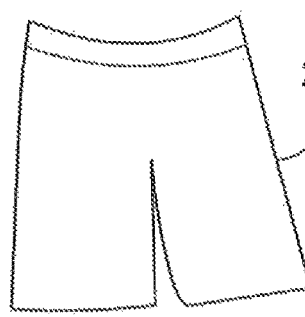
FIG. 20 is an embodiment of the present invention showing examination shorts.
Figure 21:
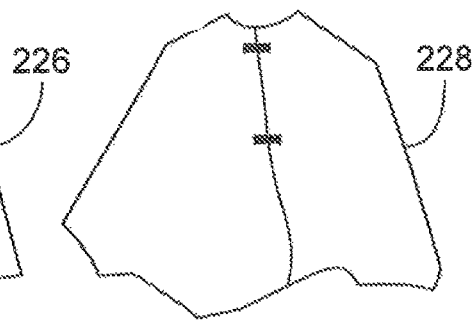
FIG. 21 is an embodiment of the present invention showing a poncho.
Figure 26:
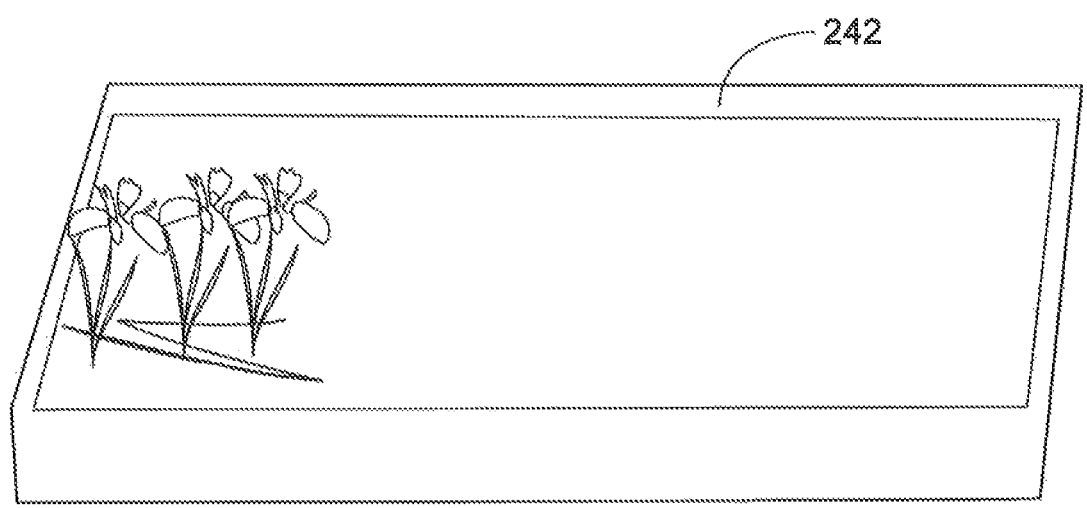
FIG. 26 is an embodiment of the present invention showing a soil liner in a flower bed or in a garden.

FIG. 11 shows a die cut bag 120, having a die cut handle 122, a coupon 124 that can be peeled off of the bag 120, and a coupon 126 that can be cut from the bag 120.

FIG. 11A shows a food storage bag 200 having food 202.

FIG. 11B shows an empty food storage bag 200.

In an embodiment the die cut bags have a width of approximately 5" to 30", a height from 5" to 30" and a gusset from 0.5" to 15", with a bag thickness of approximately 0.35 to 10.0 mil.

In an embodiment the loop handle bag has a width from about 3" to about 30", a height of 45" to about 30" and a gusset from 0.5" to 15", with a bag thickness of approximately 0.35 to 10.0 mil.

In an embodiment the tri-fold handle bag has a width from about 3" to 30", a height from 54" to 30" and a gusset from 0.5" to 15", with a bag thickness of approximately 035 to 10.0 mil.

In an embodiment the soft loop flat bag has a width of about 3" to 30" and a height from 5" to 30", with a bag thickness of approximately 035 to 10.0 mil.

In an embodiment the wave style bag has a width from about 3" to 30", a height from 5" to 30" and a gusset from 0.5" to 15", with a bag thickness of approximately 0.35 to 10.0 mil.

In an embodiment the drawstring bags have a width from about 5" to 30", a height of 5" to 30" and a gusset from 0.5" to 15", with a bag thickness of approximately 0.35 to 10.0 mil.

In an embodiment the drawstring cord bag has a width from about 5" to 30", a height of 5" to 30" and a gusset of 0.5 to15", with a bag thickness of approximately 0.35 to 10.0 mil.

In an embodiment the plastic composition comprises approximately 47-50% $CaO_3$, approximately 40% HDPE, approximately 10% LLPPE, and a filler/bonding agent of approximately 0-3%.

In an embodiment, the filler/bonding agent comprises an ester such as a long chain (waxy) aliphatic ester. In a preferred embodiment, the filler/bonding agent is a waxy substrate such as a tallow based wax.

In an embodiment the $CaCO_3$ is approximately 20-30% of the weight of the composition for the composition.

In an embodiment the HDPE and LLDPE are pre-blended and extruded into pellets.

In an embodiment approximately 35-40% CaCO₃ is used by weight for the composition of the plastic composition.

Independent lab tests done on a 1.0 mil thick Medium T-sack made with 25-35% CaCO₃, show that the T-sack performs just as well, if not better than a standard T-sack made with a polyethylene blend and approximately 5-10% CaCO₃. Tests performed include tensile strength and elongation (ASTM D882), tear resistance (ASTM D1922), and puncture force (ASTM D5748-01).

Regarding the 1.0 mil thick Medium T-sack made with 25-35% CaCO₃, the tensile strength and elongation test done in the length direction showed a maximum load ranging from 3.25 to 425 lbf, with the elongation break ranging from 325% to 400%. The tensile strength and elongation test done in the width direction showed a maximum load ranging from 2.75 to 3.0 lbf, with the elongation break ranging from 550% to 625%.

Regarding the 1.0 mil thick Medium T-sack made with 25-35% CaCO₃, the tear resistance test done in the length direction showed results ranging from 15 to 18 g. The tear resistance test done in the width direction showed results ranging from 300 to 360 g.

Regarding the 1.0 mil thick Medium T-sack made with 25-35% CaCO₃, the puncture force test done showed a maximum load ranging from 4.1 to 5.1 lbf.

The invention claimed is:

1. A single layer plastic composition comprising:
    approximately 20-49 wt. % calcium carbonate;
    approximately 30-60 wt. % high density polyethylene;
    approximately 0-20 wt. % linear low density polyethylene;
    approximately 0-10 wt. % fillers, bonding agent, or combination thereof other than said calcium carbonate;
    said single layer plastic composition consisting of a single layer;
    said single layer plastic composition further comprising a biopolymer.

2. The single layer plastic composition of claim 1 wherein said biopolymer is approximately 0.5% to 20% by weight of said single layer plastic composition.

3. The single layer plastic composition of claim 1 wherein said biopolymer is an amount less than 1.5 wt. %.

4. The single layer plastic composition of claim 1 wherein said biopolymer is selected from the group consisting of: poly lactic add, poly-hydroxybutanoate, poly-hydroxyalkanoate, Nylon 610, Nylon 611.

5. The single layer plastic composition of claim 1 wherein said single layer plastic composition contains no fibers.

6. The single layer plastic composition of claim 1 wherein said external surface of said single layer plastic composition has a smooth surface.

7. The single layer plastic composition of claim 1 wherein said single layer plastic composition provides a moisture barrier.

8. The single layer plastic composition of claim 1 wherein said single layer plastic composition is biodegradable.

9. The single layer plastic composition of claim 1 wherein said single layer has a barcode on a surface of said single layer.

10. The single layer plastic composition of claim 1 wherein said single layer has a coupon on a surface of said single layer.

11. The single layer plastic composition of claim 1 wherein said single layer plastic composition is compostable.

12. A single layer plastic composition comprising:
    approximately 20-49 wt. % mineral material;
    approximately 30-60 wt. % high density polyethylene;
    approximately 0-20 wt. % linear low density polyethylene;
    approximately 040 wt. % fillers, bonding agents, or combination thereof other than said mineral material;
    said single layer plastic composition consisting of a single layer;
    said single layer plastic composition further comprising a biopolymer.

13. The single layer plastic composition of claim 12 wherein said mineral material is selected from the group consisting of calcium carbonate, calcium sulfate, barium sulfate, kaolin, mica, zinc oxide, dolomite, glass fiber, hollow glass microbead, silica, chalk, talc, pigment, titanium dioxide, bentonite, day, zeolite, slate, diatomaceous earth and combinations thereof.

14. The single layer plastic composition of claim 12 wherein said biopolymer is approximately 0.5% to 20% by weight of said single layer plastic composition.

15. The single layer plastic composition of claim 12 wherein said biopolymer is an amount less than 1.5 wt. %.

16. The single layer plastic composition of claim 12 wherein said biopolymer is selected from the group consisting of: poly lactic add, poly-hydroxybutanoate, poly-hydroxyalkanoate, Nylon 610, Nylon 611.

17. The single layer plastic composition of claim 12 wherein said single layer plastic composition contains no fibers.

18. The single layer plastic composition of claim 12 wherein said external surface of said single layer plastic composition has a smooth surface.

19. The single layer plastic composition of claim 12 wherein said single layer plastic composition provides a moisture barrier.

20. The single layer plastic composition of claim 12 wherein said single layer plastic composition is biodegradable.

21. The simile layer plastic composition of claim 12 wherein said single layer has a barcode on a surface of said single layer.

22. The single layer plastic composition of claim 12 wherein said single layer has a coupon on a surface of said single layer.

23. The single layer plastic composition of claim 12 wherein said single layer plastic composition is compostable.

24. A single layer plastic composition comprising:
    25-40 wt. % calcium carbonate;
    30-50 wt. % high density polyethylene;
    5-15 wt. % linear low density polyethylene;
    2-7 wt. % filler, bonding agent, or combination thereof other than said calcium carbonate;
    said single layer plastic composition consisting of a single layer;
    said single layer plastic composition further comprising a biopolymer.

25. A single layer plastic composition comprising:
    approximately 20-49 wt. % mineral material;
    approximately 30-60 wt. % high density polyethylene;
    approximately 0-20 wt. % low density polyethylene, linear low density polyethylene or a combination thereof;
    approximately 040 wt. % fillers, bonding agent, or combination thereof other than said mineral material;

said single layer plastic composition consisting of a single layer;

said single layer plastic composition further comprising a biopolymer.

26. A single layer plastic composition comprising:
calcium carbonate;
high density polyethylene;
linear low density polyethylene; and
a filler, bonding agent, or combination thereof other than said calcium carbonate;
said single layer plastic composition consisting of a single layer;
said single layer plastic composition further comprising a biopolymer.

27. The single layer plastic composition of claim 26 wherein said calcium carbonate comprises less than 50% by weight of said single layer plastic composition.

28. A single layer plastic composition comprising:
calcium carbonate;
high density polyethylene;
low density polyethylene, linear low density polyethylene or a combination; and
a filler, bonding agent or combination thereof other than said calcium carbonate;
said single layer plastic composition consisting of a single layer;
said single layer plastic composition further comprising a biopolymer.

29. The single layer plastic composition of claim 28 wherein said calcium carbonate comprises less than 50% by weight of said single layer plastic composition.

30. The single layer plastic composition of claim 25 further comprising an antimicrobial component.

31. The plastic composition of claim 25 wherein said single layer plastic composition is formed into a bag, cover, sheet, protective garment, school, office or warehouse supply, storage bag, medical examination paper, bedding sheets, soil liner bubble mailer, mailing labels, protective films, stretch wrap films and tapes.

32. The single layer plastic composition of claim 25 wherein said single layer plastic composition is wound on a roll.

33. The single layer plastic composition of claim 25 wherein said single layer plastic composition is perforated.

34. The single layer plastic composition of claim 25 wherein polyethylene consists of high density polyethylene and linear low density polyethylene.

35. The single layer plastic composition of claim 26 wherein polyethylene consists of high density polyethylene, low density polyethylene and linear low density polyethylene.

36. The single layer plastic composition of claim 28 wherein polyethylene consists of high density polyethylene, low density polyethylene and linear to density polyethylene.

* * * * *